US010758276B2

(12) United States Patent
Biyani et al.

(10) Patent No.: US 10,758,276 B2
(45) Date of Patent: *Sep. 1, 2020

(54) ADJUSTABLE HEIGHT PEDICLE SCREW

(71) Applicant: GLOBUS MEDICAL, INC., Audubon, PA (US)

(72) Inventors: Ashok Biyani, Toledo, OH (US); Gary Durivage, Toledo, OH (US)

(73) Assignee: Globus Medical, Inc., Audubon, PA (US)

( * ) Notice: Subject to any disclaimer, the term of this patent is extended or adjusted under 35 U.S.C. 154(b) by 12 days.

This patent is subject to a terminal disclaimer.

(21) Appl. No.: 16/176,450

(22) Filed: Oct. 31, 2018

(65) Prior Publication Data
US 2019/0125413 A1 May 2, 2019

Related U.S. Application Data

(63) Continuation of application No. 15/056,019, filed on Feb. 29, 2016, now Pat. No. 10,117,679.

(60) Provisional application No. 62/127,030, filed on Mar. 2, 2015.

(51) Int. Cl.
A61B 17/70 (2006.01)
A61B 17/86 (2006.01)

(52) U.S. Cl.
CPC ...... A61B 17/7037 (2013.01); A61B 17/7032 (2013.01); A61B 17/8685 (2013.01)

(58) Field of Classification Search
CPC ........................................................ F16B 43/009
USPC ......................................... 411/535–536, 546
See application file for complete search history.

(56) References Cited

U.S. PATENT DOCUMENTS

| 487,721 | A | * | 12/1892 | De Kalb | F16B 31/04 411/350 |
| 5,090,855 | A | * | 2/1992 | Terry | F16B 39/24 29/525.02 |
| 5,895,189 | A | * | 4/1999 | Ruckert | F16B 5/0233 403/DIG. 1 |
| 6,719,796 | B2 | * | 4/2004 | Cohen | A61F 2/44 623/17.15 |
| 7,168,902 | B2 | * | 1/2007 | Terry | F16B 31/04 411/149 |
| 2005/0059972 | A1 | * | 3/2005 | Biscup | A61B 17/686 606/308 |
| 2006/0241593 | A1 | * | 10/2006 | Sherman | A61B 17/7032 606/278 |
| 2007/0243040 | A1 | * | 10/2007 | Chen | F16B 39/282 411/161 |
| 2010/0135748 | A1 | * | 6/2010 | Bucknell | B25B 29/02 411/535 |

(Continued)

FOREIGN PATENT DOCUMENTS

DE 3321403 A1 * 12/1984 ............ F16B 39/124
WO 2011-H65101 * 6/2011

OTHER PUBLICATIONS

English translation of DE 3221403, accessed Jan. 14, 2020.*

Primary Examiner — Jan Christopher L Merene

(57) ABSTRACT

Described herein is a pedicle screw for use in the thoracolumbar spine where the height can be adjusted intraoperatively before or after installation member of the longitudinal member. The pedicle screws with adjustable height may be made with a monoaxial or polyaxial configuration. The height of the pedicle screw can be lengthened or shortened.

14 Claims, 19 Drawing Sheets

(56) References Cited

U.S. PATENT DOCUMENTS

2011/0318140 A1* 12/2011 Chang ................... B62K 21/16
411/535

* cited by examiner

ADJUSTABLE HEIGHT PEDICLE SCREW

CROSS-REFERENCE TO RELATED APPLICATIONS

This application is a continuation of U.S. application Ser. No. 15/056,019 filed on Feb. 29, 2016, now U.S. Pat. No. 10,117,679, which claims priority to U.S. Provisional Application No. 62/127,030 filed Mar. 2, 2015, the entire disclosures of which are expressly incorporated herein by reference.

STATEMENT REGARDING FEDERALLY SPONSORED RESEARCH OR DEVELOPMENT

This invention was not made with any government support.

BACKGROUND

Spinal fusion surgery usually involves placement of pedicle screws in lumbar and thoracic spine. Pedicle screws are typically available in different length and diameter and are used for a wide variety of indications such as open conventional surgery and minimally invasive spinal surgery. Typically, a longitudinal member is fastened to two or more vertebral anchors with the help of set screws or others similar fasteners on either side of the spine. Occasionally, the height of the screws inserted in to the vertebrae does not match up, particularly if more than two screws are inserted on each side. Uneven height of the head of the pedicle screw makes it harder for installation of the longitudinal member. If such a situation is encountered, the surgeon typically addresses it by utilization of reduction tools or a washer to raise the height of the pedicle screw. Occasionally, a previously inserted pedicle screw may need to be backed out a few turns such that the longitudinal member may be well seated inside the tulip of the pedicle screw. These manures can be tedious and time consuming. Loss of fixation is also a concern if a screw has to be backed out for alignment purposes. In minimally invasive cases, height alignment of the screws is even more critical because of limited access to the hardware.

It will be advantageous to have adjustable height pedicle screws, which allow elongation or shortening such that some of the aforementioned difficulties encountered during spinal instrumentation can be mitigated.

Most current designs of pedicle screws have a fixed height of the head of the screw in relation to the screw shaft. Intraoperative height adjustment is sometimes necessary for anchoring the longitudinal members, particularly in patients requiring multi-segmental fixation. Most surgeons tend to either utilize washers or back out the pedicle screws when there is a height mismatch. Backing out the screws may compromise the quality of fixation. Additionally, it is difficult to adjust the height of the pedicle screw during minimally invasive spinal surgery with currently available devices. Finally, it may be also be advantageous to further adjust the height of the pedicle screws after placement of the longitudinal member but before final tightening of the construct.

SUMMARY

Described herein is a variable height pedicle screw that may be utilized during spinal surgery. The overall length of the pedicle screw can be lengthened or shortened.

Also, several methods of accomplishing elongation or shortening of the rod are described. The lower threaded stationary portion of the screw mounted on the vertebra is coupled with a variable height upper portion of the pedicle screw. Incremental elongation is achieved by means of a helical ramp. A combination of features such as a variable height ramp, pressure distribution ramp and a positive ratchet locator may be utilized, as disclosed in greater detail below.

Alternatively, a height adjusting sleeve is utilized in another embodiment, which engages with left hand and right hand external mounting threads of the stationary lower and variable upper components. By rotating the height adjusting sleeve, incremental elongation of the pedicle screw is accomplished.

In yet another embodiment, the variable height upper portion may telescope into the stationary threaded lower portion to accomplish overall shortening of the pedicle screw. The pedicle screw head design may be fixed or polyaxial. One or more lugs may be utilized to facilitate forced rotation and height adjustment of the pedicle screw.

Further, in several situations where the longitudinal member is well seated within the head, it may be advantageous to alter the height of the vertebral anchors after rod installation. One example of such a situation would be further reduction of residual deformity in patients with spondylolisthesis after hardware installation, whereby the height of the distal vertebral pedicle screw can be elongated, forcing further improvement in vertebral alignment.

In another instance during scoliosis surgery, residual rotational deformity is frequently left after installation of hardware. By elongating the height of the pedicle screw on the convex side of the deformity after hardware installation, the surgeon would be able to achieve further derotation. In a similar manner, a vertebral height could be shortened on the concave side of the deformity. In this setting, the pedicle screws are pulled towards the longitudinal member by collapsing the screw height, thus enabling further rotatory correction.

In particular embodiments, the pedicle screw includes: a longitudinal screw portion; and, an adjustable height component that is capable of being co-axially and adjustable affixed to the longitudinal screw portion, and that is capable of being axially adjusted intraoperatively with respect to the longitudinal screw portion.

In certain embodiments, the height of the adjustable height component is capable of being adjusted intraoperatively before or after installation of the longitudinal screw portion.

In certain embodiments, the adjustable height screw component includes an internally threaded portion capable of accepting a polyaxial screw or a monoaxial screw.

In certain embodiments, the polyaxial screw or monoaxial is configured for accepting a rod compression screw.

In certain embodiments, the height adjustable component has at least one positive ratchet locator for incremental height adjustment.

In certain embodiments, the pedicle screw further includes a variable height engagement ramp.

In certain embodiments, the variable height component ramp is positioned at an end of the longitudinal screw portion that is adjacent to the adjustable height component.

In certain embodiments, the variable height component ramp is at an end of the adjustable height component that is adjacent to the longitudinal screw portion. In a particular embodiment, the adjustable height component includes a positive stop is configured to engage a portion of variable height component ramp.

In certain embodiments, the variable height component ramp is capable of being coaxially positioned at an end of the longitudinal screw portion that is adjacent to the adjustable height component.

In certain embodiments, wherein the variable height component ramp further includes a pressure distribution ramp.

In certain embodiments, the polyaxial screw has an external polyaxial pivot head, and wherein the adjustable height component includes an internal polyaxial locator capable of accepting the external polyaxial pivot head on the polyaxial screw.

In certain embodiments, the longitudinal screw portion has a smooth or threaded shank for allowing the adjustable height component to be moved co-axially with respect to the longitudinal screw portion.

In certain embodiments, pedicle screw further includes a lug capable of being adjusted for forced rotation and height adjustment of the adjustable height component.

BRIEF DESCRIPTION OF THE FIGURES

Component call out—it is to be understood that components having the same element may have the same number for ease of explanation herein.

Item #1 One piece mounting attachment stationary screw with mounting thread
Item #2 Fine pitch left hand external mounting thread
Item #3 Height adjusting sleeve-type component
Item #4 Fine pitch right hand internal thread
Item #5 Fine pitch left hand internal thread
Item #6 Spanner adjusting lug
Item #7 Fine pitch right hand external thread
Item #8 Upper rod holder with external thread
Item #9 Internal mounting threads
Item #10 Final internal rod locating locator
Item #11 Rod compression screw
Item #12 Polyaxial compression threads
Item #13 Polyaxial compression screw
Item #14 Polyaxial tightening face
Item #15 External polyaxial pivot head
Item #16 Mounting attachment stationary screw with polyaxial head
Item #17 Fine pitch left hand external thread component
Item #18 Internal polyaxial locator
Item #19 Lower polyaxial cradle
Item #20 Polyaxial compression tightener
Item #21 Compression tightener compressor
Item #22 Internal compression thread
Item #23 Adjusting lug
Item #24 External compression thread
Item #25 Mounting attachment stationary screw with rotary head
Item #26 Upper smooth portion of attachment screw
Item #27 Upper threaded portion of attachment screw optional
Item #28 Engagement head of attachment screw
Item #29 Lower variable height swivel component
Item #30 Variable height engagement ramp
Item #31 Internal thread for polyaxial screw
Item #32 External thread for polyaxial screw
Item #33 Polyaxial screw
Item #34 Positive stop
Item #35 Upper variable height component
Item #36 Counterbored retainer
Item #37 Mounting attachment stationary screw with lower variable height
Item #38 Indexing ratchet
Item #39 Pressure distribution ramp

DESCRIPTION OF THE PREFERRED EMBODIMENTS

Figure 1:
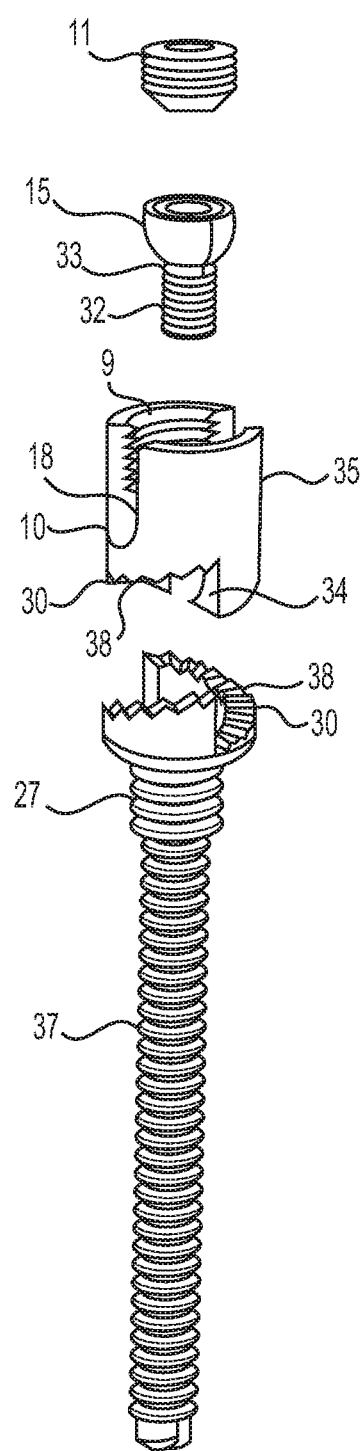
FIG. 1. Exploded, perspective assembly view of a first embodiment of an adjustable height pedicle screw having a positive ratchet locator.

FIG. 1 shows an exploded assembly view of the variable height with positive ratchet locator. The variable height adjustment screw assembly allows the height of the final installed alignment rod (not shown) to be incrementally adjusted due to required height variations. With this design the mounting attachment stationary screw with lower variable height 37 is rotated to achieve the required height. The mounting attachment stationary screw with lower variable eight 37 is mounted inside the bone. There is an optional upper threaded portion of attachment screw 27 that can provide additional mounting strength if required. The mounting attachment stationary screw with lower variable height 37 has a variable height engagement ramp 30 with optional indexing ratchets 38 that allow for incremental height adjustments when the upper variable height component 35 is engaged with its respective variable height engagement ramp 30 with optional indexing ratchets 38. There is a positive stop 34 that will maintain a minimum retracted height engagement with the stationary screw with lower variable height 37 and the upper variable height component 35. There is an internal polyaxial locator pocket 18 in the upper variable height component 35 that will accept the external polyaxial pivot head 15 on the polyaxial screw 33. The polyaxial screw 33 has polyaxial screw external threads 32 that will engage in internal threads located in the mounting attachment stationary screw with lower variable height 37 near the area of the attachment screw 27. When the desired position with the mounting attachment stationary screw with lower variable height 37 and the upper variable height component 35 is achieved the polyaxial screw 33 is tightened. At this time the alignment rod not shown can be placed into the final internal rod locating locator 10 that is in the upper variable height component 35. The rod compression screw 11 can be tightened in the internal mounting threads 9 that are located in the upper variable height component 35. The alignment rod not shown will be tightened between the rod compression screw 11 and the final internal rod locating locator 10.

Figure 2:
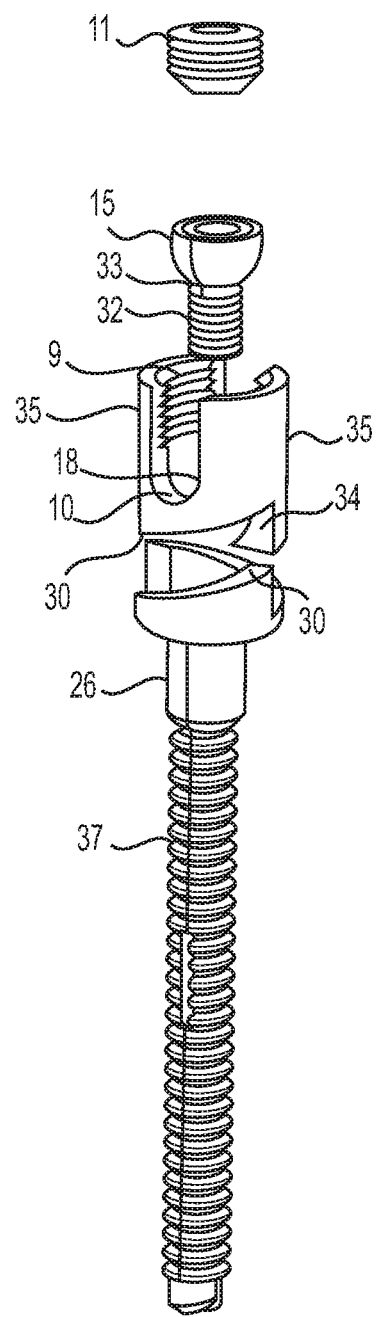
FIG. 2. Exploded perspective assembly view of another embodiment of an adjustable height pedicle screw having a variable height ramp.

Referring now to FIG. 2, it shows an exploded assembly view of the variable height with variable height ramp. The variable height adjustment screw assembly allows the height of the final installed alignment rod (not shown) to be infinitely adjusted due to required height variations. With this design the mounting attachment stationary screw with lower variable height 37 is rotated to achieve the required height. The mounting attachment stationary screw with lower variable height 37 is mounted inside the bone. There is an optional upper smooth portion of attachment screw 26 that can allow less upper gripping if required. The mounting attachment stationary screw with lower variable height 37 has a variable height engagement ramp 30 that allows for infinitely variable height adjustments when the upper variable height component 35 is engaged with its respective variable height engagement ramp 30. There is a positive stop 34 that will maintain a minimum retracted height engagement with the stationary screw with lower variable height 37 and the upper variable height component 35. There is an internal polyaxial locator pocket 18 in the upper variable height component 35 that will accept the external polyaxial pivot head 15 on the polyaxial screw 33. The polyaxial screw 33 has polyaxial screw external threads 32 that will engage in internal threads located in the mounting attachment stationary screw with lower variable height 37 near the area of the attachment screw 26. When the desired position with the mounting attachment stationary screw with lower variable height 37 and the upper variable height component 35 is achieved the polyaxial screw 33 is tightened. At this time, the alignment rod (not shown) can be placed into the final internal rod locating locator 10 that is in the upper variable height component 35. The rod compression screw 11 can be tightened in the internal mounting threads 9 that are located in the upper variable height component 35. The alignment rod (not shown) will be tightened between the rod compression screw 11 and the final internal rod locating locator 10.

Figure 3:
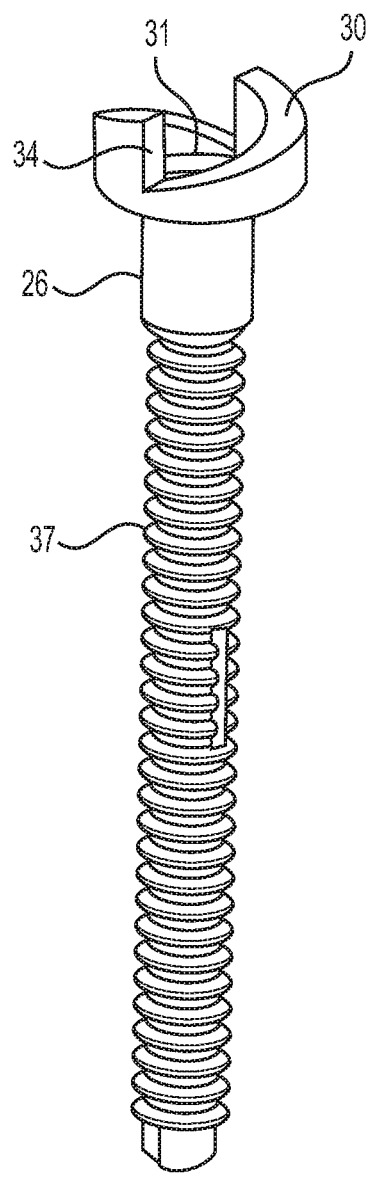
FIG. 3. Rotated view of a mounting attachment stationary screw with lower variable height for the embodiment shown in FIG. 2.

Referring now to FIG. 3, a rotated view of the mounting attachment stationary screw with lower variable height is shown for clarity purposes. With this design the mounting attachment stationary screw with lower variable height 37 is rotated to achieve the required height. The mounting attachment stationary screw with lower variable height 37 is mounted inside the bone. There is an optional upper smooth portion of attachment screw 26 that can allow less upper gripping if required. The mounting attachment stationary screw with lower variable height 37 has a variable height engagement ramp 30 that allows for infinitely variable height adjustments when the upper variable height component 35 (not shown for clarity purposes) is engaged with its respective variable height engagement ramp 30. There is a positive stop 34 that will maintain a minimum retracted height engagement with the stationary screw with lower variable height 37 and the upper variable height component 35 not shown for clarity purposes. There is an internal thread for polyaxial screw 31 located in the mounting attachment stationary screw with lower variable height 37 near the area of the attachment screw 26.

Figure 4:
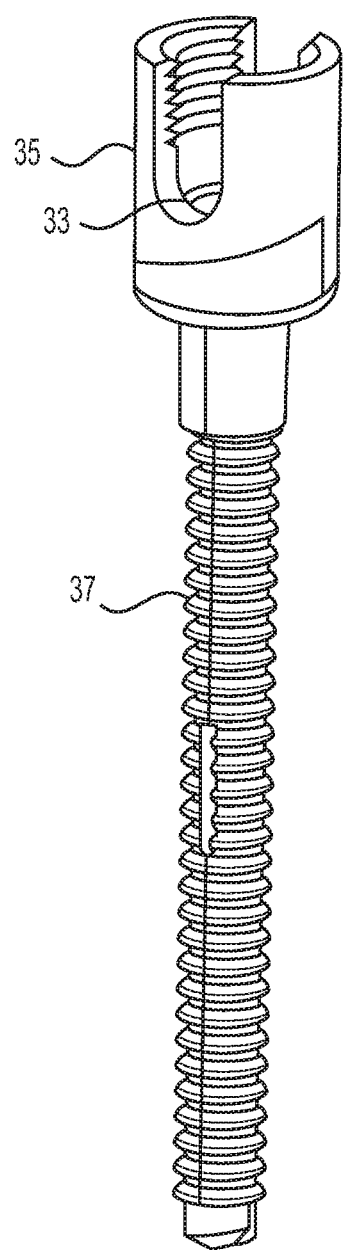
FIG. 4. Assembly view of the variable ramp height non-rotating version in the retracted position for the embodiment shown in FIG. 2.

FIG. 4 shows an assembly view of the variable ramp height non-rotating version in the retracted position. The screw is omitted for clarity. The variable height adjustment screw assembly allows the height of the final installed alignment rod (not shown) to be infinitely adjusted due to required height variations. With this design the mounting attachment stationary screw with lower variable height 37 is rotated to achieve the required height. The mounting attachment stationary screw with lower variable height 37 is engaged with the upper variable height component 35. The components are aligned as required and joined together with the polyaxial screw 33.

Figure 5:
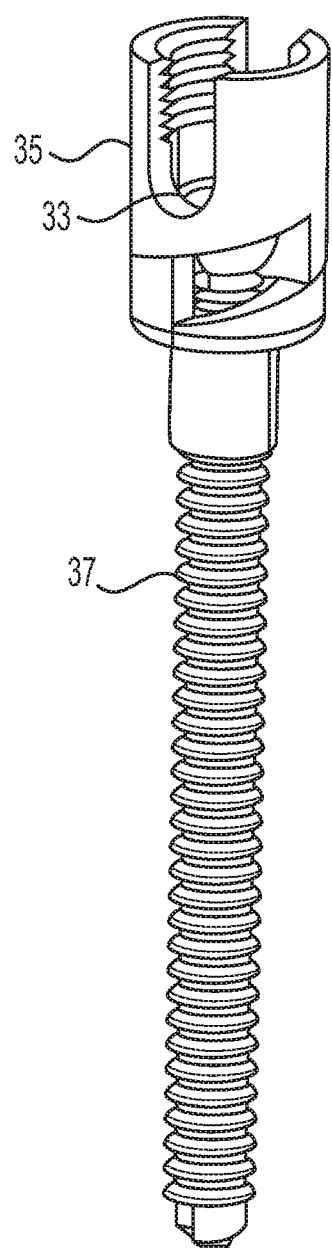
FIG. 5. Assembly view of the variable ramp height non-rotating version in the extended position for the embodiment shown in FIG. 2.

FIG. 5 shows an assembly view of the variable ramp height non-rotating version in the extended position. The screw is omitted for clarity. The variable height adjustment screw assembly allows the height of the final installed alignment rod (not shown) to be infinitely adjusted due to required height variations. With this design the mounting attachment stationary screw with lower variable height 37 is rotated to achieve the required height. The mounting attachment stationary screw with lower variable height 37 is engaged with the upper variable height component 35. The components are aligned as required and joined together with the polyaxial screw 33.

Figure 6:
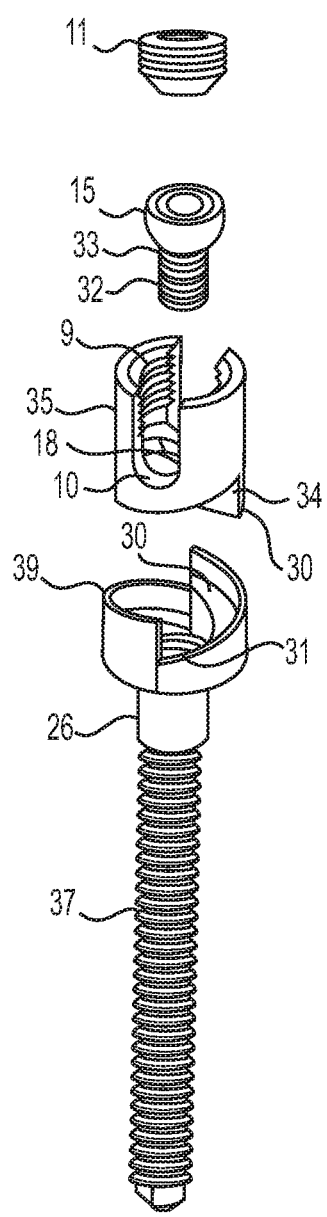
FIG. 6. Exploded, perspective assembly view of another embodiment of an adjustable height pedicle screw having a variable height ramp and the pressure distribution ramp.

FIG. 6 demonstrates an exploded assembly view of the variable height with variable height ramp and the pressure distribution ramp. The variable height adjustment screw assembly allows the height of the final installed alignment rod (not shown) to be infinitely adjusted due to required height variations. With this design the mounting attachment stationary screw with lower variable height 37 is rotated to achieve the required height. The mounting attachment stationary screw with lower variable height 37 is mounted inside the bone. There is an optional upper smooth portion of attachment screw 26 that can allow less upper gripping if required. The mounting attachment stationary screw with lower variable height 37 has a variable height engagement ramp 30 that allows for infinitely variable height adjustments when the upper variable height component 35 is engaged with its respective variable height engagement ramp 30. There is a positive stop 34 that will maintain a minimum retracted height engagement with the stationary screw with lower variable height 37 and the upper variable height component 35. There is an internal polyaxial locator pocket 18 in the upper variable height component 35 that will accept the external polyaxial pivot head 15 on the polyaxial screw 33. The polyaxial screw 33 has polyaxial screw external threads 32 that will engage in internal thread for polyaxial screw 31 located in the mounting attachment stationary screw with lower variable height 37 near the area of the attachment screw 26. When the desired position with the mounting attachment stationary screw with lower variable height 37 and the upper variable height component 35 is achieved the polyaxial screw 33 is tightened. There is an optional pressure distribution ramp 39 that runs parallel with the engagement ramp 30. Any adjusted height variation is done in coordination with the optional pressure distribution ramp 39. The optional pressure distribution ramp 39 is part of the mounting attachment stationary screw with lower variable height 37. At this time the alignment rod (not shown) can be placed into the final internal rod locating locator 10 that is in the upper variable height component 35. The rod will also have even distribution on the optional pressure distribution ramp 39 and the final internal rod locating locator 10. This will evenly distribute the applied pressure. The rod compression screw 11 can be tightened in the internal mounting threads 9 that are located in the upper variable height component 35. The alignment rod (not shown) will be tightened between the rod compression screw 11 and the final internal rod locating locator 10 and the optional pressure distribution ramp 39.

Figure 7:
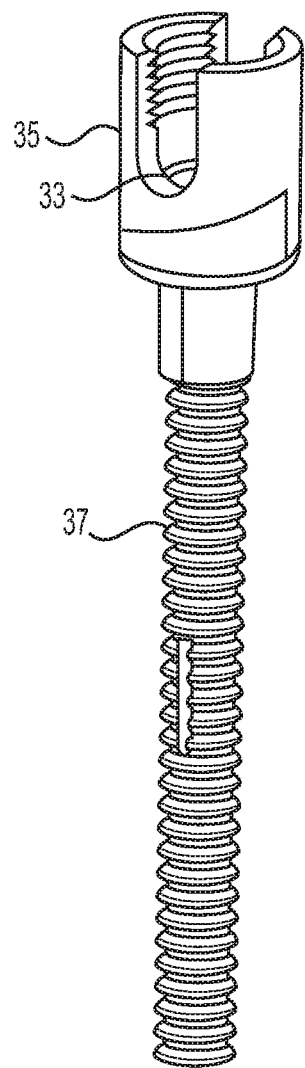
FIG. 7. Assembly view of the variable ramp height non-rotating version with the pressure distribution ramp in the retracted position for the embodiment shown in FIG. 6.

FIG. 7 shows an assembly view of the variable ramp height non-rotating version with the pressure distribution ramp in the retracted position. The screw is omitted for clarity. The variable height adjustment screw assembly allows the height of the final installed alignment rod (not shown) to be infinitely adjusted due to required height variations. With this design the mounting attachment stationary screw with lower variable height 37 is rotated to achieve the required height. The mounting attachment stationary screw with lower variable height 37 is engaged with the upper variable height component 35. The components are aligned as required and joined together with the polyaxial screw 33. There is an optional pressure distribution ramp 39 that distributes the applied pressure from the alignment rod (not shown).

Figure 8:
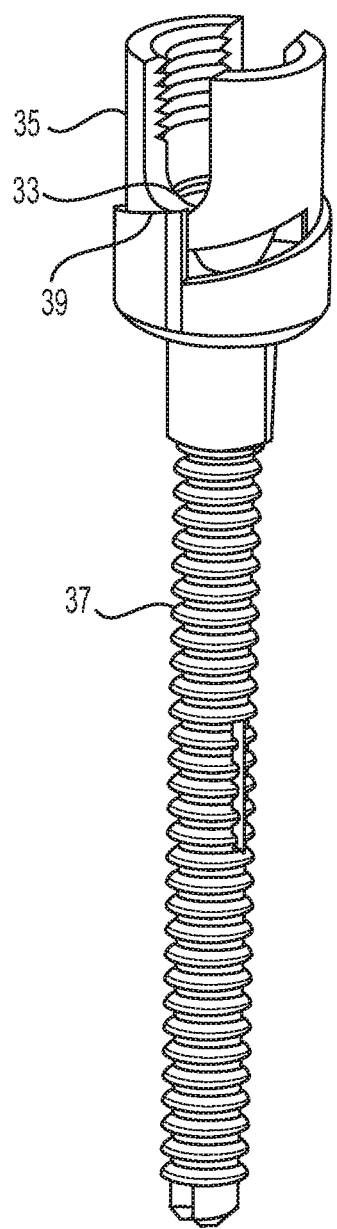
FIG. 8. Assembly view of the variable ramp height non-rotating version with the pressure distribution ramp in the extended position for the embodiment shown in FIG. 6.

Referring now to FIG. 8, an assembly view of the variable ramp height non-rotating version with the pressure distribution ramp in the extended position is shown. The screw is omitted for clarity. The variable height adjustment screw assembly allows the height of the final installed alignment rod (not shown) to be infinitely adjusted due to required height variations. With this design the mounting attachment stationary screw with lower variable height 37 is rotated to achieve the required height. The mounting attachment stationary screw with lower variable height 37 is engaged with the upper variable height component 35. The components are aligned as required and joined together with the polyaxial screw 33. There is an optional pressure distribution ramp 39 that distributes the applied pressure from the alignment rod (not shown).

Figure 9:
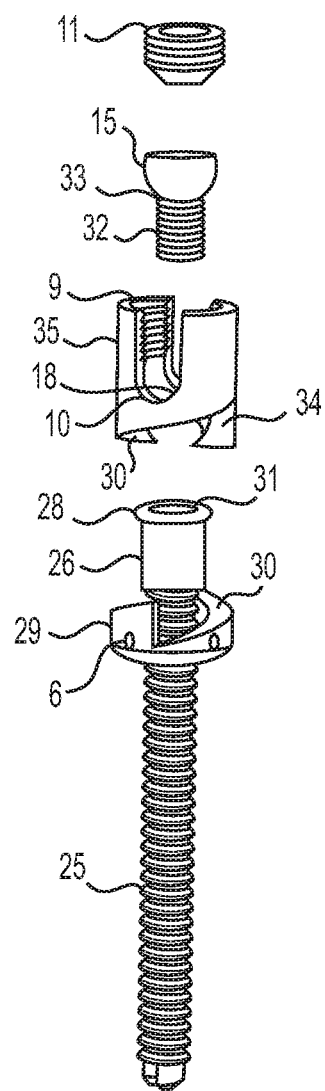
FIG. 9. Exploded, perspective assembly view of another embodiment of an adjustable height pedicle screw having a variable height ramp with a lower swivel ramp.

FIG. 9 shows an exploded assembly view of the variable height with variable height ramp with lower swivel ramp. The variable height adjustment screw assembly allows the height of the final installed alignment rod (not shown) to be infinitely adjusted due to required height variations. With this design the lower variable height swivel component 29 is rotated to achieve the required height. There are optional singular or multiple spanner adjusting lug 6 can be used for rotating the lower variable height swivel component 29. The optional singular or multiple spanner adjusting lug 6 can be applied to any varied design. The lug will allow for easier forced rotation. The mounting attachment stationary screw with rotary head 25 is placed inside the lower variable height swivel component 29. The mounting attachment stationary screw with rotary head 25 is then mounted inside the bone. There is an engagement head of attachment screw 28 on the end of the mounting attachment stationary screw with rotary head 25. There is a counterbored retainer in the lower variable height swivel component 29 that accepts the engagement head of attachment screw 28. When this is engaged the lower variable height swivel component 29 is able to rotate about the axis of the engagement head of attachment screw 28. There is an optional upper smooth portion of attachment screw 26 that can allow less upper gripping if required. The lower variable height swivel component 29 has a variable height engagement ramp 30 that allows for infinitely variable height adjustments when the upper variable height component 35 is engaged with its respective variable height engagement ramp 30. There is a positive stop 34 that will maintain a minimum retracted height engagement with the lower variable height swivel component 29 and the upper variable height component 35. There is an internal polyaxial locator pocket 18 in the upper variable height component 35 that will accept the external polyaxial pivot head 15 on the polyaxial screw 33. The polyaxial screw 33 has polyaxial screw external threads 32 that will engage in internal thread for polyaxial screw 31 located in the mounting attachment stationary screw with rotary head 25 near the area of the attachment screw 26. When the desired position with the lower variable height swivel component 29 and the upper variable height component 35 is achieved the polyaxial screw 33 is tightened. At this time the alignment rod (not shown) can be placed into the final internal rod locating locator 10 that is in the upper variable height component 35. The rod compression screw 11 can be tightened in the internal mounting threads 9 that are located in the upper variable height component 35. The alignment rod (not shown) will be tightened between the rod compression screw 11 and the final internal rod locating locator 10.

Figure 10:
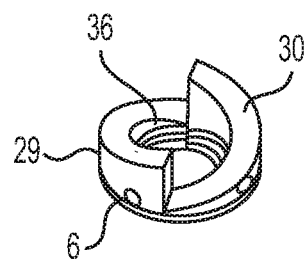
FIG. 10. Rotated view of the lower swivel ramp for the embodiment shown in FIG. 9.

Referring now to FIG. 10, a rotated view of the lower swivel ramp is shown separately for clarity. The lower variable height swivel component 29 is rotated to achieve the required height. There are optional singular or multiple spanner adjusting lug 6 can be used for rotating the lower variable height swivel component 29. The optional singular or multiple spanner adjusting lug 6 can be applied to any varied design. The lug will allow for easier forced rotation. The mounting attachment stationary screw with rotary head 25 not shown for clarity purposes is placed inside the lower variable height swivel component 29. On the end of the mounting attachment stationary screw with rotary head 25 not shown for clarity purposes there is a counterbored retainer 36 in the lower variable height swivel component 29 that accepts the engagement head of attachment screw 28 not shown for clarity purposes.

Figure 11:
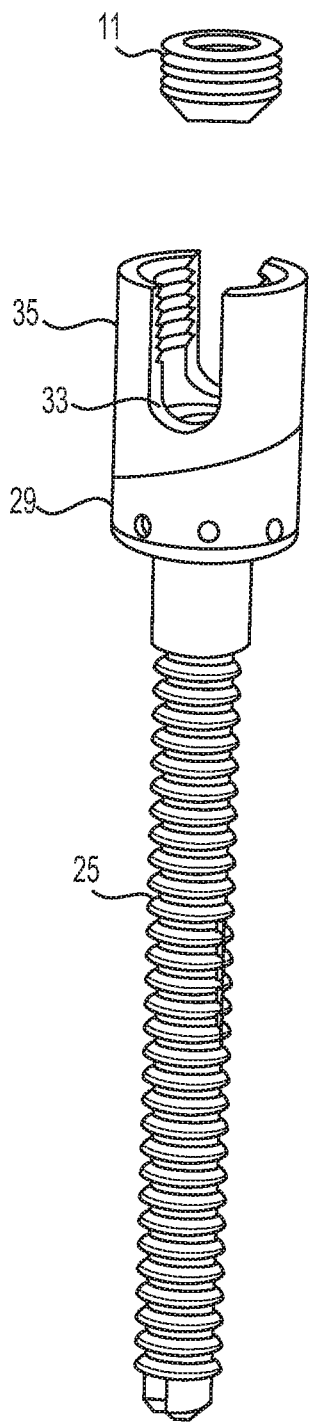
FIG. 11. Assembly view of the variable ramp height rotating version with the swivel in the retracted position for the embodiment shown in FIG. 9.

FIG. 11 shows an assembly view of the variable ramp height rotating version with the swivel in the retracted position. The variable height adjustment screw assembly allows the height of the final installed alignment rod (not shown) to be infinitely adjusted due to required height variations. With this design the mounting attachment stationary screw with rotary head 25 has a lower variable height swivel component 29 that is rotated to achieve the required height. The mounting attachment stationary screw with rotary head 25 is engaged with the upper variable height component 35. The components are aligned as required and joined together with the polyaxial screw 33. The alignment rod (not shown) can be placed into the final internal rod locating locator that is in the upper variable height component 35. The rod compression screw 11 can be tightened against the alignment rod (not shown) to complete the assembly.

Figure 12:
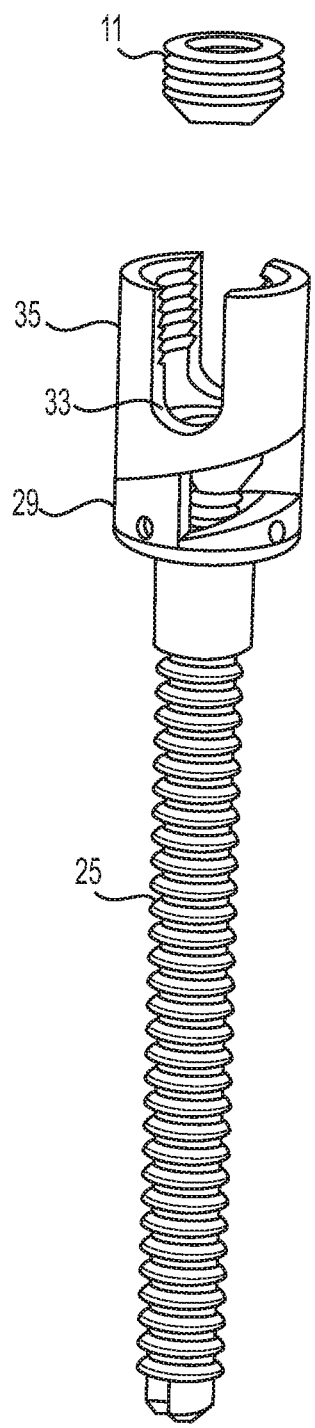
FIG. 12. Assembly view of the variable ramp height rotating version with the swivel in the extended position for the embodiment shown in FIG. 9.

FIG. 12 shows an assembly view of the variable ramp height rotating version with the swivel in the extended position. The variable height adjustment screw assembly allows the height of the final installed alignment rod (not shown) to be infinitely adjusted due to required height variations. With this design the mounting attachment stationary screw with rotary head 25 has a lower variable height swivel component 29 that is rotated to achieve the required height. The mounting attachment stationary screw with rotary head 25 is engaged with the upper variable height component 35. The components are aligned, as required, and joined together with the polyaxial screw 33. The alignment rod (not shown) can be placed into the final internal rod locating locator that is in the upper variable height component 35. The rod compression screw 11 can be tightened against the alignment rod (not shown) to complete the assembly.

The variable height adjustment screw assembly allows the height of the final installed alignment rod (not shown) to be infinitely adjusted due to required height variations. With this design the mounting attachment stationary screw with rotary head 25 has a lower variable height swivel component 29 that is rotated to achieve the required height. The mounting attachment stationary screw with rotary head 25 is engaged with the upper variable height component 35. The components are aligned as required and joined together with the polyaxial screw 33. The alignment rod (not shown) can be placed into the final internal rod locating locator that is in the upper variable height component 35. The rod compression screw 11 can be tightened against the alignment rod (not shown) to complete the assembly.

Figure 13:
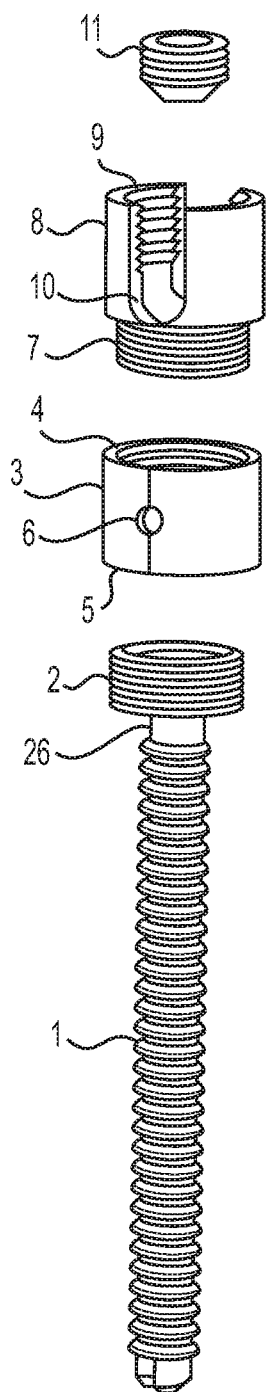
FIG. 13. Exploded, perspective assembly view of a telescoping variable height nonrotating embodiment of an adjustable height pedicle screw.

Referring to FIG. 13, it shows an exploded assembly view of the telescoping variable height non-rotating version. The telescoping variable height adjustment screw assembly allows the height of the final installed alignment rod (not shown) to be infinitely adjusted due to required height variations. With this design the height adjusting sleeve 3 is rotated to achieve the required height. The one piece mounting attachment stationary screw with mounting thread 1 is mounted inside the bone. There is an optional upper smooth portion of attachment screw 26 that can allow less upper gripping if required. The pitch and the direction of the telescoping threads can vary however they must match up with the corresponding component as well as being reversed with the adjacent threads in order to properly function. The fine external mounting thread 2 must correspond with the internal thread 5 and be opposite direction of the external thread 7 that must correspond with the internal thread 4. The one piece mounting attachment stationary screw with mounting thread 1 has a fine pitch left hand external mounting thread 2 that will be engaged with the fine pitch left hand internal thread 5 on the end of the height adjusting sleeve 3 while at the same time the upper rod holder with external thread 8 with the fine pitch right hand external thread 7 will be engaged with the fine pitch right hand internal thread 4 on the end of the height adjusting sleeve 3. It is desirable to have enough thread engagement for durability. When the height adjusting sleeve 3 is rotated the components will extend or retract depending on the rotation that is applied with the height adjusting sleeve 3. On the perimeter of the height adjusting sleeve 3 there are optional singular or multiple spanner adjusting lug 6 that can be applied to any varied design. The lug will allow for easier forced rotation about it respective axis. When the proper required height is achieved with the height adjusting sleeve 3 the alignment rod (not shown) can be placed into the final internal rod locating locator 10 that is in the upper rod holder with external thread 8. The rod compression screw 11 can be tightened in the internal mounting threads 9 that are located in the upper rod holder with external thread 8. The alignment rod (not shown) will be tightened between the rod compression screw 11 and the final internal rod locating locator 10. When the alignment rod (not shown) is placed into more than one assembly with the upper rod holder with external thread 8 the height adjusting sleeve 3 can be adjusted into the final desired position. A fine thread jam screw (not shown) can be installed to lock the final location.

Figure 14:
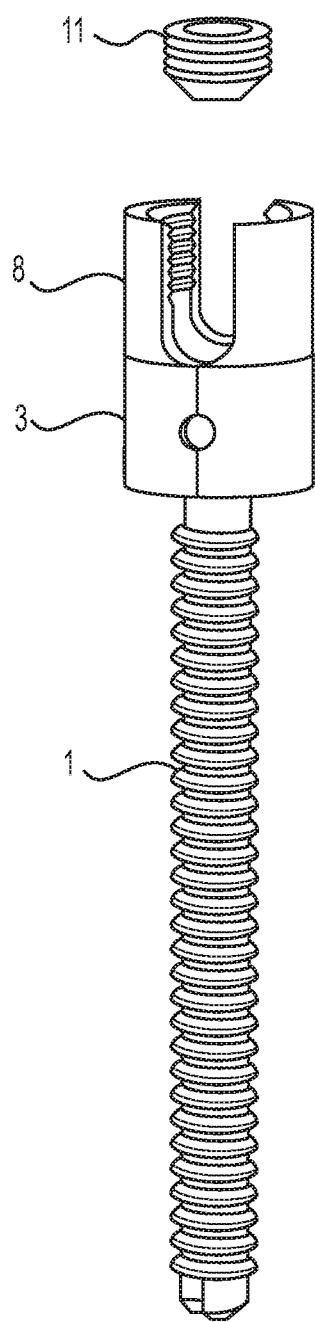
FIG. 14. Assembly view of the telescoping variable height non-rotating version in the retracted position for the embodiment shown in FIG. 13.

FIG. 14 shows an assembly view of the telescoping variable height non-rotating version in the retracted position. The one piece mounting attachment stationary screw with mounting thread 1 is engaged with the height adjusting sleeve 3 while engaged at the same time with the upper rod holder with external thread 8. When the proper required height is achieved with the height adjusting sleeve 3 the alignment rod (not shown) can be placed into the final internal rod locating locator. The rod compression screw 11 will be tightened compressing the alignment rod (not shown) between the rod compression screw 11 and the final internal rod locating locator.

Figure 15:
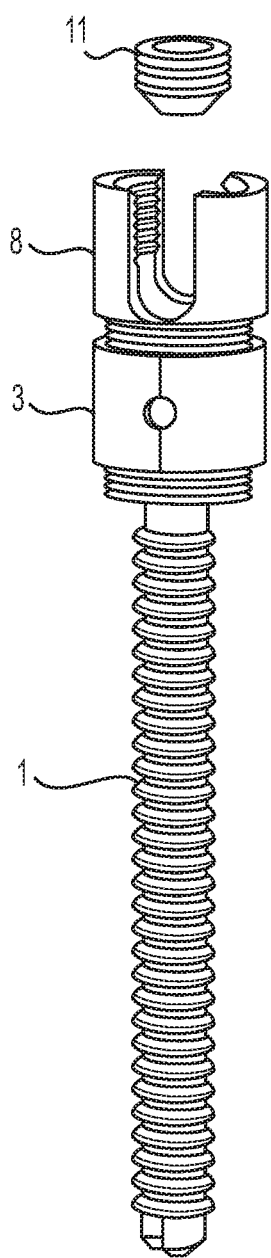
FIG. 15. Assembly view of the telescoping variable height non-rotating version in the extended position for the embodiment shown in FIG. 13.

FIG. 15 shows an Assembly view of the telescoping variable height non-rotating version in the extended position. The one piece mounting attachment stationary screw with mounting thread 1 is engaged with the height adjusting sleeve 3 while engaged at the same time with the upper rod holder with external thread 8. When the proper required height is achieved with the height adjusting sleeve 3 the alignment rod (not shown) can be placed into the final internal rod locating locator. The rod compression screw 11 will be tightened compressing the alignment rod (not shown) between the rod compression screw 11 and the final internal rod locating locator.

Figure 16:
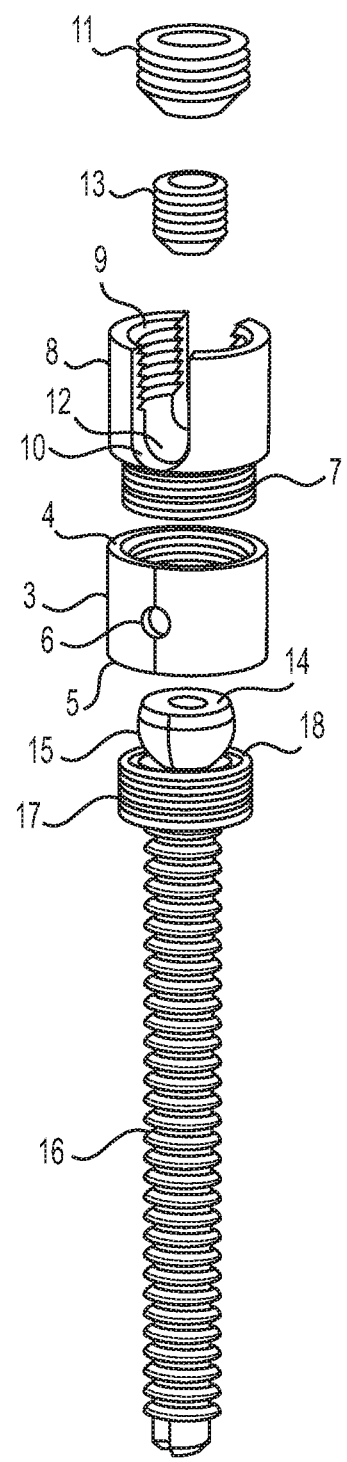
FIG. 16. Exploded, perspective assembly view of a telescoping variable height polyaxial rotating embodiment of an adjustable height pedicle screw.

FIG. 16 shows an exploded assembly view of the telescoping variable height polyaxial rotating version. The telescoping variable height adjustment screw assembly allows the height of the final installed alignment rod (not shown) to be infinitely adjusted due to required height variations as well as polyaxial. With this design the height adjusting sleeve 3 is rotated to achieve the required height. The mounting attachment stationary screw with polyaxial head 16 is placed inside of the fine pitch left hand external thread base component 17. The mounting attachment stationary screw with polyaxial head 16 is mounted inside the bone. There is an internal polyaxial locator pocket 18 located in the fine pitch left hand external thread base component 17. This internal polyaxial locator pocket 18 will accept and locate the external polyaxial pivot head 15. The pitch and the direction of the telescoping threads can vary however they must match up with the corresponding component as well as being reversed with the adjacent threads in order to properly function. The fine external mounting thread 2 must correspond with the internal thread 5 and be opposite direction of the external thread 7 that must correspond with the internal thread 4. The one piece mounting attachment stationary screw with mounting thread 1 has a fine pitch left hand external mounting thread 2 that will be engaged with the fine pitch left hand internal thread 5 on the end of the height adjusting sleeve 3 while at the same time the upper rod holder with external thread 8 with the fine pitch right hand external thread 7 will be engaged with the fine pitch right hand internal thread 4 on the end of the height adjusting sleeve 3. It is desirable to have enough thread engagement for durability. When the height adjusting sleeve 3 is rotated the components will extend or retract depending on the rotation that is applied with the height adjusting sleeve 3. On the perimeter of the height adjusting sleeve 3 there are optional singular or multiple spanner adjusting lug 6 that can be applied to any varied design. The lug will allow for easier forced rotation about it respective axis. When the proper required height is achieved with the height adjusting sleeve 3 the assembly must be tightened utilizing the polyaxial compression screw 13 into the polyaxial internal compression threads 12. The applied force from the polyaxial compression screw 13 will press against the polyaxial tightening face 14. This will maintain the infinitely variable desired polyaxial angle. The alignment rod (not shown) can then be placed into the final internal rod locating locator 10 that is in the upper rod holder with external thread 8. The rod compression screw 11 can be tightened in the internal mounting threads 9 that are located in the upper rod holder with external thread 8. The alignment rod (not shown) will be tightened between the rod compression screw 11 and the final internal rod locating locator 10. When the alignment rod (not shown) is placed into more than one assembly with the upper rod holder with external thread 8 the height adjusting sleeve 3 can be adjusted into the final desired position.

Figure 17:
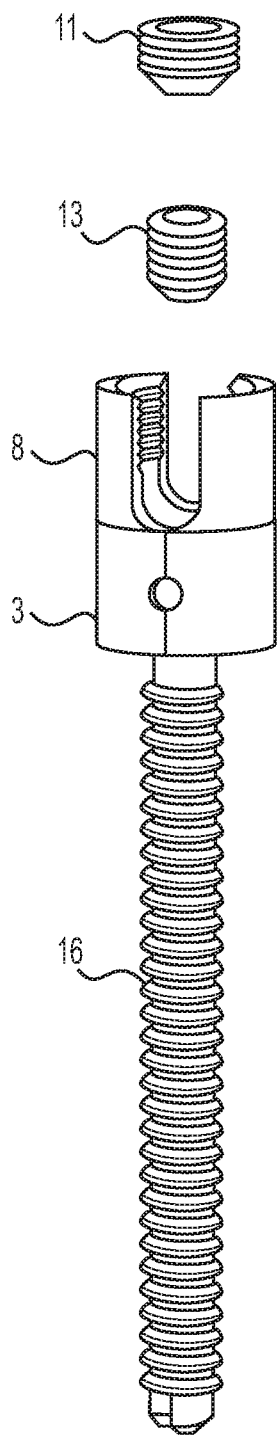
FIG. 17. Assembly view of the telescoping variable height polyaxial rotating version in the retracted position for the embodiment shown in FIG. 1.

FIG. 17 shows an assembly view of the telescoping variable height polyaxial rotating version in the retracted position. The mounting attachment stationary screw with polyaxial head 16 is placed inside of the fine pitch left hand external thread base component 17. The fine pitch left hand external thread base component 17 is engaged with the height adjusting sleeve 3 while engaged at the same time with the upper rod holder with external thread 8. When the proper required height is achieved with the height adjusting sleeve 3 the polyaxial compression screw 13 is tightened maintaining the infinitely variable desired polyaxial angle. The alignment rod (not shown) can be placed into the final internal rod locating locator. The rod compression screw 11 will be tightened compressing the alignment rod (not shown) between the rod compression screw 11 and the final internal rod locating locator.

Figure 18:
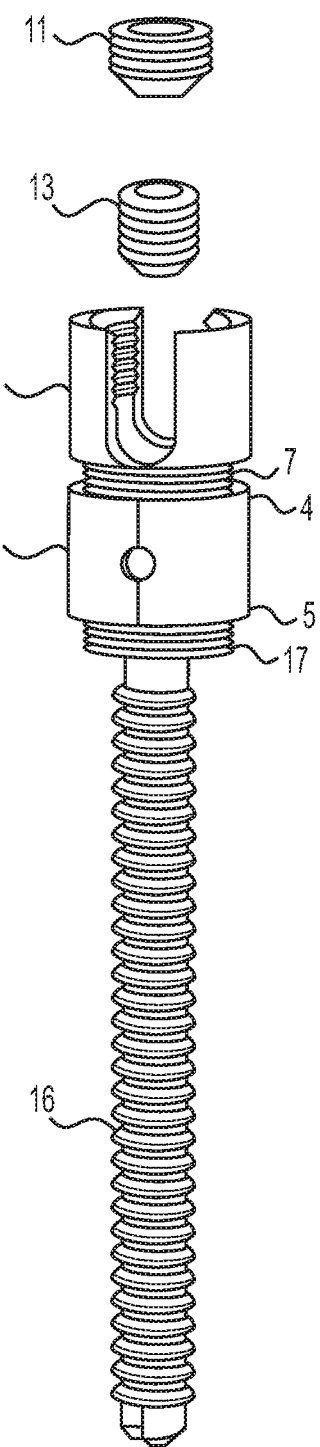
FIG. 18. Assembly view of the telescoping variable height polyaxial rotating version in the extended position for the embodiment shown in FIG. 16.

FIG. 18 shows an assembly view of the telescoping variable height polyaxial rotating version in the extended position. The mounting attachment stationary screw with polyaxial head 16 is placed inside of the fine pitch left hand external thread base component 17. The fine pitch left hand external thread base component 17 is engaged with the height adjusting sleeve 3 while engaged at the same time with the upper rod holder with external thread 8. When the proper required height is achieved with the height adjusting sleeve 3 the polyaxial compression screw 13 is tightened maintaining the infinitely variable desired polyaxial angle. The alignment rod (not shown) can be placed into the final internal rod locating locator. The rod compression screw 11 will be tightened compressing the alignment rod (not shown) between the rod compression screw 11 and the final internal rod locating locator.

Figure 19:
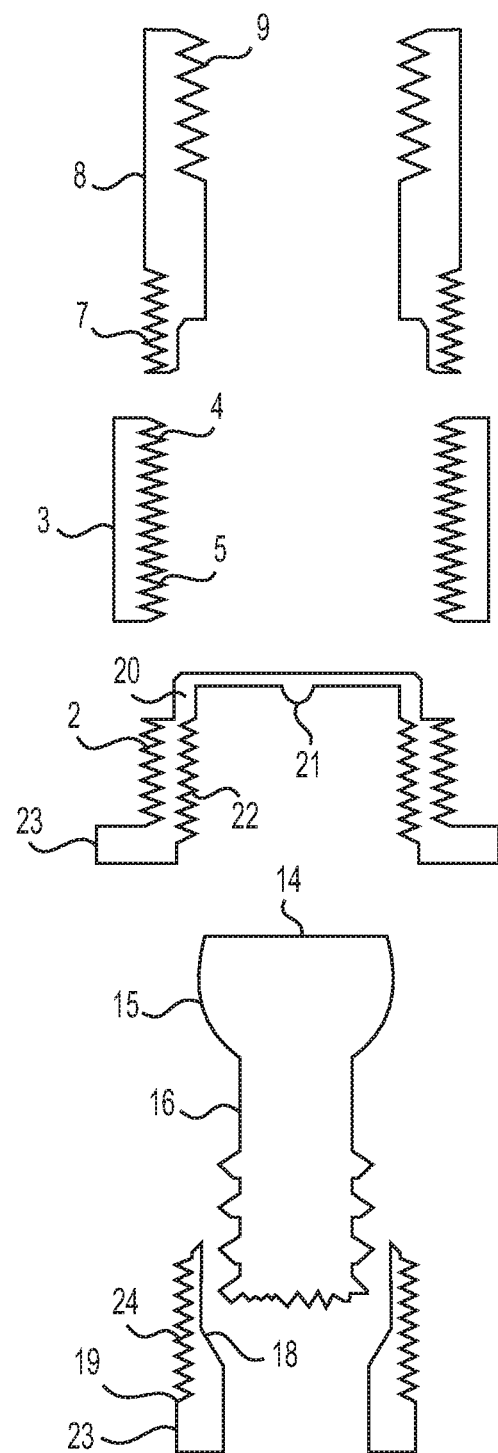
FIG. 19. Exploded, perspective assembly view of a telescoping variable height compression polyaxial rotating embodiment of an adjustable height pedicle screw the screw is omitted for clarity.

FIG. 19 shows an exploded assembly view of the telescoping variable height compression polyaxial rotating version the screw is omitted for clarity. The telescoping variable height adjustment screw assembly allows the height of the final installed alignment rod (not shown) to be infinitely adjusted due to required height variations as well as polyaxial. With this design the height adjusting sleeve 3 is rotated to achieve the required height. The mounting attachment stationary screw with polyaxial head 16 is placed inside of the lower polyaxial cradle 19. The mounting attachment stationary screw with polyaxial head 16 is mounted inside the bone. There is an internal polyaxial locator pocket 18 located in the lower polyaxial cradle 19. The internal polyaxial locator pocket 18 will accept and locate the external polyaxial pivot head 15. There are optional singular or multiple adjusting lug 23 located on the lower perimeter on the lower polyaxial cradle 19 that will allow for easier forced rotation about it respective axis. There is a polyaxial compression tightener 20 that compresses the polyaxial tightening face 14 on the mounting attachment stationary screw with polyaxial head 16 against the compression tightener compressor 21 on the polyaxial compression tightener 20. This occurs when the internal compression thread 22 has full thread engagement and tightened against the external compression thread 24 on the lower polyaxial cradle 19. There are optional singular or multiple adjusting lug 23 located on the lower perimeter of the polyaxial compression tightener 20 that will allow for easier forced rotation about it respective axis.

When tightened, this will maintain the infinitely variable desired polyaxial angle. The pitch and the direction of the telescoping threads can vary however they must match up with the corresponding component as well as being reversed with the adjacent threads in order to properly function. The fine external mounting thread 2 must correspond with the internal thread 5 and be opposite direction of the external thread 7 that must correspond with the internal thread 4. The polyaxial compression tightener 20 has a fine pitch left hand external mounting thread 2 that will be engaged with the fine pitch left hand internal thread 5 on the end of the height adjusting sleeve 3 while at the same time the upper rod holder with external thread 8 with the fine pitch right hand external thread 7 will be engaged with the fine pitch right hand internal thread 4 on the end of the height adjusting sleeve 3. It is desirable to have enough thread engagement for durability. When the height adjusting sleeve 3 is rotated the components will extend or retract depending on the rotation that is applied with the height adjusting sleeve 3. On the perimeter of the height adjusting sleeve 3 there are optional singular or multiple spanner adjusting lug 6 that can be applied to any varied design. The lug will allow for easier forced rotation about it respective axis. When the proper required height is achieved with the height adjusting sleeve 3, the alignment rod (not shown) can then be placed into the final internal rod locating locator that is in the upper rod holder with external thread 8. The rod compression screw 11 can be tightened in the internal mounting threads 9 that are located in the upper rod holder with external thread 8. The alignment rod (not shown) will be tightened between the rod compression screw (not shown) and the final internal rod locating locator. When the alignment rod (not shown) is placed into more than one assembly with the upper rod holder with external thread 8 the height adjusting sleeve 3 can be adjusted into the final desired position. A fine thread jam screw (not shown) can be installed to lock the final location.

Figure 20:
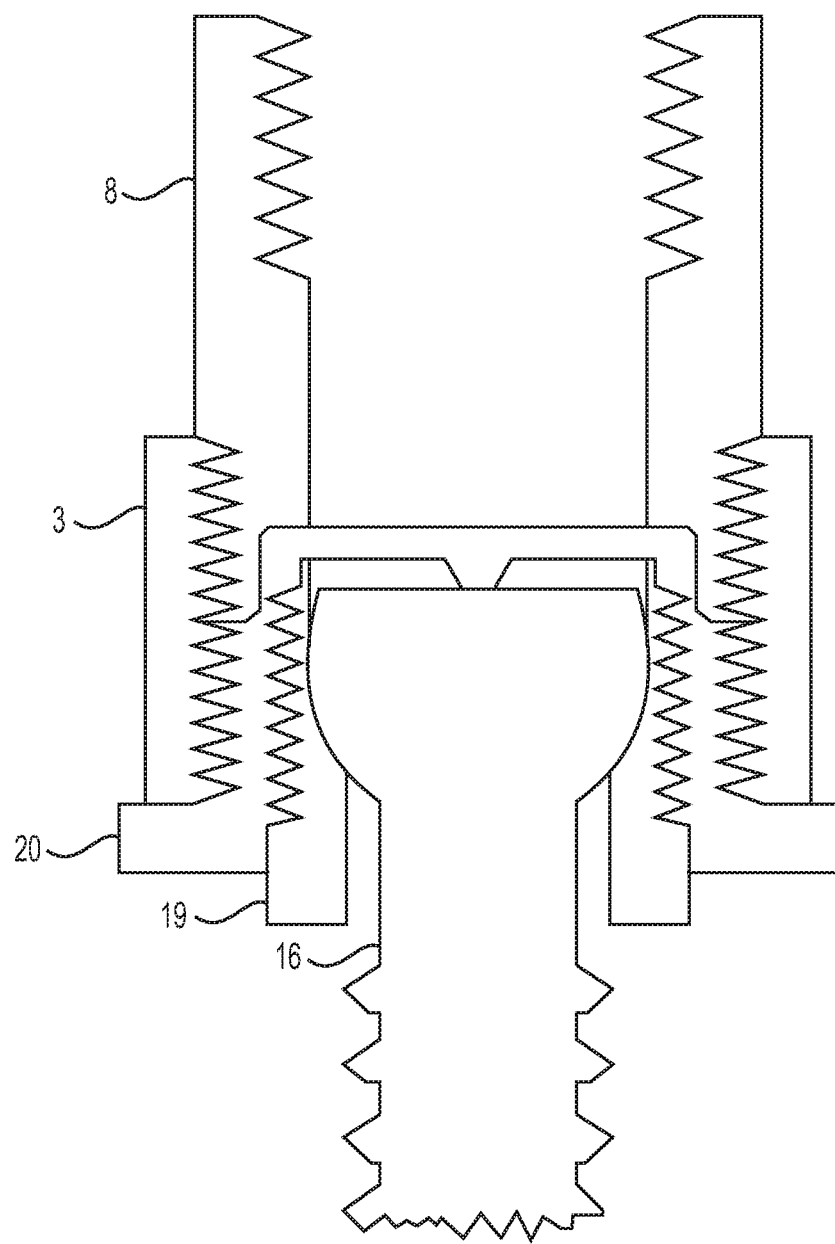
FIG. 20. Assembly view of the telescoping variable height compression polyaxial rotating version for the embodiment shown in FIG. 20 the screw is omitted for clarity.

Referring to FIG. 20, an assembly view of the telescoping variable height compression polyaxial rotating version the screw is omitted for clarity is shown. The mounting attachment stationary screw with polyaxial head 16 is placed inside of the lower polyaxial cradle 19. The mounting attachment stationary screw with polyaxial head 16 is mounted inside the bone. There is a polyaxial compression tightener 20 that compresses the mounting attachment stationary screw with polyaxial head 16 against the polyaxial compression tightener 20. When the required angle is achieved the polyaxial compression tightener 20 is tightened against the lower polyaxial cradle 19.

The fine pitch left hand external thread polyaxial compression tightener 20 is engaged with the height adjusting sleeve 3 while engaged at the same time with the upper rod holder with external thread 8. When the proper required height is achieved the alignment rod (not shown) can be placed into the final internal rod locating locator. The rod compression screw 11 will be tightened compressing the alignment rod (not shown) between the rod compression screw 11 and the final internal rod locating locator. A fine thread jam screw (not shown) can be installed to lock the final location.

The above detailed description of the present invention is given for explanatory purposes. It will be apparent to those skilled in the art that numerous changes and modifications other than those cited can be made without departing from the scope of the invention. Accordingly, the whole of the foregoing description is to be construed in an illustrative and not an imitative sense, the scope of the invention being defined solely by the appended claims.

The invention claimed is:

1. A pedicle screw for spinal fixation, comprising:
a longitudinal screw comprising a threaded portion and a variable height engagement ramp immovably and permanently disposed as an angled top surface of the longitudinal screw located at a proximal end of the longitudinal screw; and
an adjustable height component having an angled bottom surface and disposed on top of the variable height engagement ramp in slidable contact with the angled top surface, wherein the adjustable height component is capable of being adjustably affixed to the longitudinal screw, and capable of being axially adjusted intraoperatively with respect to the longitudinal screw,
wherein the angled bottom surface and the angled top surface are in non-threaded contact and slidable with respect to each other to adjust a height of the adjustable height component,
wherein the variable height engagement ramp further includes a pressure distribution ramp.

2. The pedicle screw of claim 1, wherein the height of the adjustable height component is capable of being adjusted intraoperatively before or after installation of the longitudinal screw.

3. The pedicle screw of claim 1, wherein the longitudinal screw includes an internally threaded portion capable of accepting a polyaxial screw or a monoaxial screw to affix the adjustable height component to the longitudinal screw.

4. The pedicle screw of claim 3, wherein the adjustable height component is configured for accepting a rod compression screw.

5. The pedicle screw of claim 3, wherein the polyaxial screw has an external polyaxial pivot head, and wherein the adjustable height component includes an internal polyaxial locator capable of accepting the external polyaxial pivot head on the polyaxial screw.

6. The pedicle screw of claim 1, wherein the variable height engagement ramp has an outer diameter that is substantially equal to an outer diameter of the adjustable height component.

7. The pedicle screw of claim 6, wherein the angled top surface of the variable height engagement ramp is adapted to be positioned to face the angled bottom surface of the adjustable height component.

8. The pedicle screw of claim 1, wherein the adjustable height component includes a positive stop configured to engage a portion of variable height engagement ramp.

9. The pedicle screw of claim 6, wherein the variable height engagement ramp is integrally formed at an end of the longitudinal screw that is adjacent to the adjustable height component.

10. The pedicle screw of claim 1, wherein the longitudinal screw has a smooth or threaded shank for allowing the adjustable height component to be moved co-axially with respect to the longitudinal screw.

11. A pedicle screw for spinal fixation, comprising:
a longitudinal screw comprising a threaded portion and a variable height engagement ramp immovably and permanently disposed as an angled top surface of the longitudinal screw located at a proximal end of the longitudinal screw; and
an adjustable height component having an angled bottom surface and disposed on top of the variable height engagement ramp in slidable contact with the angled top surface, wherein the adjustable height component is capable of being adjustably affixed to the longitudinal screw, and capable of being axially adjusted intraoperatively with respect to the longitudinal screw,
wherein the angled bottom surface and the angled top surface are in non-threaded contact and slidable with respect to each other to adjust a height of the adjustable height component, wherein the height adjustment component includes a lug capable of being adjusted for forced rotation and height adjustment of the adjustable height component.

12. The pedicle screw of claim 11, wherein the longitudinal screw includes an internally threaded portion capable of accepting a polyaxial screw or a monoaxial screw to affix the adjustable height component to the longitudinal screw.

13. The pedicle screw of claim 12, wherein the adjustable height component is configured for accepting a rod compression screw.

14. The pedicle screw of claim 12, wherein the polyaxial screw has an external polyaxial pivot head, and wherein the adjustable height component includes an internal polyaxial locator capable of accepting the external polyaxial pivot head on the polyaxial screw.

* * * * *